(12) United States Patent
Märzendorfer

(10) Patent No.: US 7,607,833 B2
(45) Date of Patent: Oct. 27, 2009

(54) METHOD FOR OPERATING A MEDICAL IMAGE APPARATUS TO CORRECT FOR DEFLECTION OF THE PATIENT SUPPORT BOARD

(75) Inventor: Walter Märzendorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 17 days.

(21) Appl. No.: 11/314,134

(22) Filed: Dec. 21, 2005

(65) Prior Publication Data

US 2006/0184012 A1 Aug. 17, 2006

(30) Foreign Application Priority Data

Dec. 21, 2004 (DE) .................. 10 2004 061 591

(51) Int. Cl.
*H05G 1/00* (2006.01)
*A61B 6/04* (2006.01)
*A61B 5/05* (2006.01)

(52) U.S. Cl. .................. 378/209; 378/208; 600/426

(58) Field of Classification Search .................. 378/62, 378/63, 208–210, 4–20, 95, 163, 164, 65; 600/425, 426; 5/601, 607, 81.1 HS; 382/131, 382/132, 287–289, 291
See application file for complete search history.

(56) References Cited

U.S. PATENT DOCUMENTS

| 4,233,507 | A | * | 11/1980 | Volz | 378/18 |
|---|---|---|---|---|---|
| 5,117,829 | A | * | 6/1992 | Miller et al. | 600/427 |
| 5,537,454 | A | * | 7/1996 | Korver, II | 378/65 |
| 5,872,829 | A | * | 2/1999 | Wischmann et al. | 378/164 |
| 6,050,724 | A | * | 4/2000 | Schmitz et al. | 378/205 |
| 6,416,219 | B1 | | 7/2002 | Pflaum et al. | |
| 7,359,746 | B2 | * | 4/2008 | Arata | 600/424 |
| 2002/0081008 | A1 | * | 6/2002 | Wollenweber | 382/131 |
| 2002/0122575 | A1 | * | 9/2002 | Vaisburd et al. | 382/131 |
| 2002/0186819 | A1 | * | 12/2002 | Proksa | 378/207 |
| 2002/0188194 | A1 | * | 12/2002 | Cosman | 600/426 |
| 2003/0031301 | A1 | * | 2/2003 | Longton et al. | 378/209 |
| 2003/0088179 | A1 | * | 5/2003 | Seeley et al. | 600/424 |
| 2004/0199072 | A1 | * | 10/2004 | Sprouse et al. | 600/424 |
| 2005/0002550 | A1 | * | 1/2005 | Jabri et al. | 382/131 |
| 2005/0054915 | A1 | * | 3/2005 | Sukovic et al. | 600/424 |
| 2005/0085710 | A1 | * | 4/2005 | Earnst et al. | 600/411 |
| 2005/0113681 | A1 | * | 5/2005 | DeFreitas et al. | 600/426 |
| 2006/0093093 | A1 | * | 5/2006 | Chao et al. | 378/207 |

OTHER PUBLICATIONS

"Handbook of Medical Imaging," Sonlca et al., SPIE 2000, Vol. 2, Chapter 8, Image Registration, pp. 449-513.
"Medical Image Processing and Analysis: Handbook of Medical Imaging," vol. 2, Chapter 8, Image Registration (2000), pp. 449-513.

* cited by examiner

*Primary Examiner*—Edward J Glick
*Assistant Examiner*—Anastasia Midkiff
(74) *Attorney, Agent, or Firm*—Schiff Hardin LLP

(57) ABSTRACT

In a method for operation of an imaging medical apparatus, a recumbent board supporting an examination subject is positioned in the scan region of the medical-technical apparatus, an exposure of both a section of the recumbent board and of a part of the tissue of the examination subject to be examined in the scan region is generated, the acquired real position of the section of the recumbent board is compared with an expected position of the recumbent board by image evaluation of the exposure generated with the medical-technical apparatus, and the exposure generated with the medical-technical apparatus of the examined tissue is corrected using the expected-real comparison of the position of the recumbent board.

11 Claims, 2 Drawing Sheets

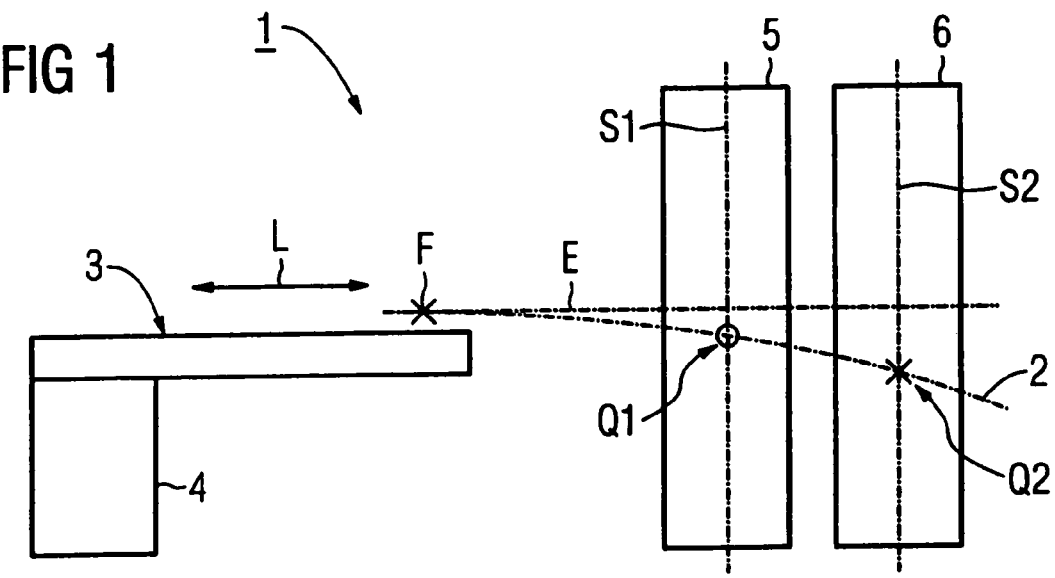
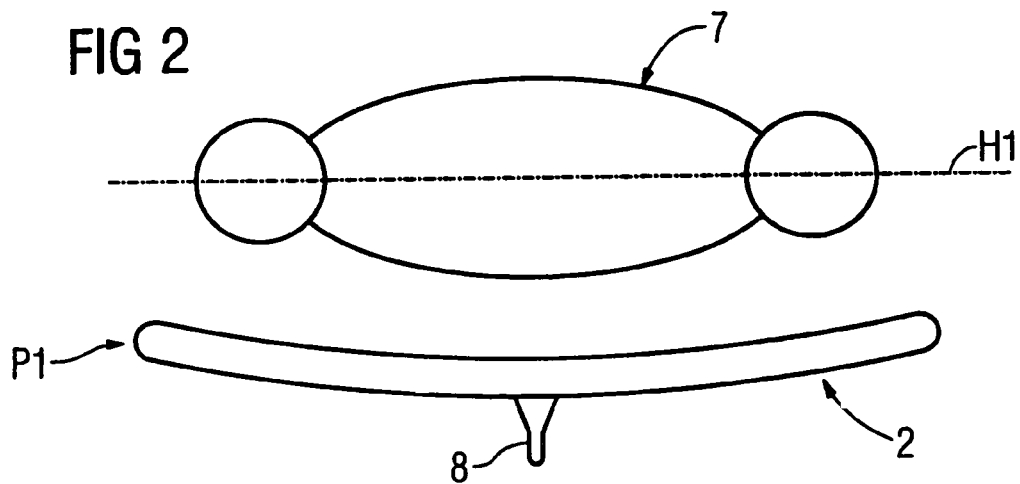
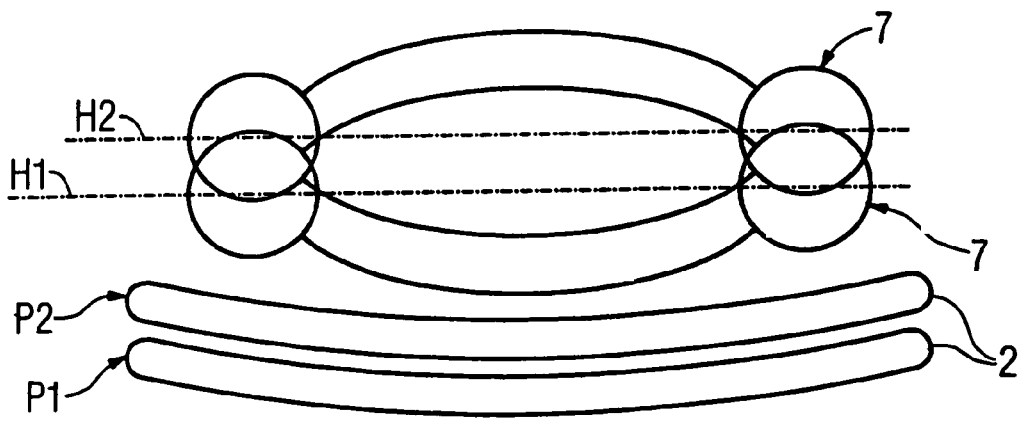

METHOD FOR OPERATING A MEDICAL IMAGE APPARATUS TO CORRECT FOR DEFLECTION OF THE PATIENT SUPPORT BOARD

BACKGROUND OF THE INVENTION

1. Field of the Invention

The present invention concerns a method for operation of a medical imaging apparatus, of the type wherein an examination subject (in particular a patient) is located on a recumbent board.

2. Description of the Prior Art

An imaging diagnostic device with a recumbent board is, for example, known from DE 199 20 008 A1.

In medical imaging methods, for example computed tomography, a patient located on a recumbent board is frequently displaced relative to a scan region of a diagnostic apparatus during the examination. In many cases, the recumbent board is supported only at one end, such that it inevitably bends with increasing forward displacement of the recumbent board. The deflection cannot be completely avoided even with a recumbent board that is designed to minimize instability. A minimization of the deflection of the recumbent board can in fact be achieved by providing the board with a multi-sided support, but this requires an elaborate track design for the movement mechanism.

As long as only a single data (image) acquisition is undertaken in a specific cross-section plane of the tissue to be examined, a slight deflection of the recumbent board is not of concern in some cases. By contrast, exact knowledge of the position (in particular also the height position) of the recumbent board is of great importance when either various exposures of the same tissue region must be superimposed, and/or when three-dimensional data are to be generated from exposures in various cross-section planes. The latter applies both in the case of separate exposures in various cross-section planes and in cases in which a continuous feed ensues during the imaging diagnosis, for example in spiral computed tomography. Radiation therapy is a field of application in which an exact association of medical imaging data with the position of the examined tissue in the examination subject is of particular importance.

SUMMARY OF THE INVENTION

An object of the present invention is to provide a method for the operation of an imaging medical apparatus that supplies particularly good spatial information of the examined tissue in a simple manner.

The above object is achieved in accordance with the present invention by a method for operating a medical imaging apparatus wherein a recumbent board is horizontally supported with an examination subject thereon, in the scan region of a medical apparatus, and an exposure of the section of the board and at least a portion of tissue of the examination subject are obtained with the medical apparatus, in which both the tissue and the section of the board are detectable. The exposure is electronically analyzed and a real position of the section of the board is thereby identified, and this real position is automatically electronically compared with the expected position to identify any deviation of the real position from the expected position, due to loading of the board. The exposure is then automatically electronically modified to correct for any detection deviation.

An examination subject (for example a patient or a tissue sample) is examined with an imaging medical apparatus (for example an apparatus operating with x-ray radiation or magnetic resonance). The examination subject is positioned on a recumbent board, which is spatially variable relative to a scan region of the medical-technical apparatus. Movement of the recumbent board and/or movement of components of the medical-technical apparatus or of the entire medical-technical apparatus thus are possible. An exposure both of a section of the recumbent board and at least one part of the tissue to be examined is generated in the scan region.

It is significant that the tissue to be examined as well as the recumbent board (at least in part) are recognizable in one and the same exposure. The desired position of the recumbent board in the scan region, i.e. that position that the recumbent board would occupy without a mechanical load, is designated as an expected value. The real position of the recumbent board under a mechanical load in the scan region deviates from the expected position. The load is due to the inherent weight of the recumbent board as well as due to the weight load of the examination subject. This expected real deviation is determined by an image evaluation of the medical-technical exposure. Correction data are determined from this evaluation that allow a modified exposure to be created that represents a fictitious exposure that would result if the position of the recumbent board were to coincide with the expected value.

Geometric data of the examined tissue thus are not used for correction of the image data, but rather geometric data of the recumbent board are used. This has the advantage that a significantly more precise correction can ensue since the geometry data regarding the examined tissue are invariable. Elaborate reinforcements of the recumbent board that could easily lead to artifact formations in the exposure created with the medical-technical apparatus therefore can be foregone. Likewise, support on both sides of the recumbent board is not required.

A requirement for the implementation of the method is that the recumbent board can be recognized in the diagnosis method implemented with the medical-technical apparatus. Insofar as the bearing (supporting) material of the recumbent board cannot be detected or can be detected only in a limited manner in the medical-technical apparatus, the unlimited application capability of the method is achieved by introducing a material into the recumbent board, or attaching a material to the board, that produces or increases the detection capability of the recumbent board. In the simplest case, the material provided to increase the detection capability is uniformly distributed in the recumbent board. For example, in the case of a magnetic resonance (MR) system, MR signal-emitting material can be added to the recumbent board. Alternatively, it is also possible to form markings on or in the recumbent board that are composed of the material increasing the detection capability. This is also applicable in MR apparatuses. Suitable PET or SPECT markers can be attached on the recumbent board in a similar manner in the case of PET (positron emission spectroscopy) or SPECT (single photon emission computed tomography) examinations.

Even in cases in which the recumbent board can be sufficiently detected in the imaging diagnostic method without additional materials, the spatial determination can be improved by designing the recumbent board with geometric structures (for example profile elements) that can be detected in the image evaluation. These profile elements preferably have the function of length scales, and can be provided in two or three spatial directions. Moreover, the profile elements can have a static function, namely to counteract the deflection of the recumbent board. In this manner it is possible to determine the exact position of the recumbent board in space without additional measurements, solely using the medical imaging method that is employed for the medical diagnosis. Insofar as the recumbent board has additional materials increasing the detection capability, these materials preferably are attached to the profile structures or form the profile structures. The profile structures can exhibit any geometric shape, for example the shape of bars, grooves, punctiform elevations or depressions as well as multidimensional rasters.

The spatial resolution of the exposure generated with the medical-technical apparatus is typically below 1 mm. By the precise detection of the position of the recumbent board by means of image evaluation (if applicable supported by markings on it in the recumbent board), the positioning of the recumbent board and thus the patient or another examination subject as well, can be determined with a comparable precision. This high spatial resolution is particularly of use in radiation therapy planning. Advantages likewise result in interventional, procedures, for example intravascular interventions, biopsies and ablations that are implemented using previously-acquired image data. In such cases, the patient is initially moved into the scan region of an imaging diagnostic and/or subsequently removed from this region again in order to effect the intervention with image-controlled navigation. The navigation is thereby based on data that were previously acquired in an altered positioning of the patient. The intervention can be implemented with high precision due to the correlation (determined by the inventive method) between the position of the patient bed and the position of the relevant tissue region. It is assumed that the position of the patient relative to the recumbent board does not change during the examination as well as the subsequent intervention. This can be achieved in a typical manner by using rigid fixation frames made from metal or carbon or with vacuum mattresses.

In a preferred embodiment, the diagnosis is implemented with two different medical-technical apparatuses. These can each be an apparatus for imaging diagnostics, with the detection capability of the recumbent board in one diagnosis method being more pronounced than in the other diagnosis method. In the inventive method both medical-technical apparatuses are positioned such that a first section of the recumbent board can be arranged in the scan region of the first medical-technical apparatus and a second section of the recumbent board can simultaneously be arranged in the scan region of the second medical-technical apparatus. In the scan region of the first medical-technical apparatus, the position of the corresponding section of the recumbent board can be detected without further measures, i.e. solely with the exposure acquired with this apparatus. By contrast, the second medical-technical apparatus supplies no evaluable information, or scant evaluable information, regarding the position of the recumbent board.

Despite errors or at least limited detection capability of the recumbent board in the second medical-technical apparatus, a measurement of the position of the recumbent board in this apparatus with methods independent of the diagnosis method (perhaps via reflection measurement) can be foregone. Rather, the position of the recumbent board is indirectly determined by assuming the directly measured position in the scan region of the first medical-technical apparatus, and the position in the scan region of the second medical-technical apparatus is determined by calculation under consideration of the mechanical properties of the recumbent board. The calculation can be based on known material properties of the recumbent board and/or on experimentally-acquired data regarding the deflection of the recumbent board.

The correction of the image data of the acquired tissue ensues as a last step of the inventive method, independently of whether the real position of the recumbent board was previously directly determined in the diagnostic method or, if applicable, was determined indirectly by a calculated interpolation or extrapolation using the second diagnostic apparatus. In the simplest case, the generated exposure is merely to be shifted linearly. It is also possible to shift image data (in particular a cross-section exposure) three-dimensionally in space depending on the actual deviation of the real position of the recumbent board from its desired position. An unintended inclination of the recumbent board in the scan region around the vertical or transverse axis, for example, can be easily, automatically detected by the width or thickness of the recumbent board being shown distorted (namely too large) in the exposure.

If diagnostic exposures of various cross-section regions of the tissue to be examined are continuously or discontinuously generated, three-dimensional data of the examined tissue can be generated from these exposures. The geometric precision of these data depend on, among other things, to what extent the recumbent board is moved with constant speed relative to the medical-technical apparatus. If the recumbent board or the medical-technical apparatus (in the case of what is known as a gliding gantry) moves in a non-uniform manner, this causes a corresponding distortion of the acquired three-dimensional image data as a result. This distortion can be compensated according to a further embodiment of the inventive method wherein the position of the recumbent board in the movement direction relative to the scan region is determined by evaluation of the diagnostic exposure as described above. For this purpose, the recumbent board has suitable markings that are detectable in the diagnostic exposure, the markings either being an integral component of the bearing structure of the recumbent board or additional marking elements. The time of each exposure can likewise be determined. Despite a possible non-uniform feed movement, a 3D data set thus can be generated that reproduces the actual geometry of the examined tissue.

An advantage of the invention is that the absolute position of a patient bed (and therewith also of the examined tissue) can be determined in space from raw or image data of an imaging medical-technical apparatus (for example a computer tomograph) without further spatial measurement. The spatial determination is particularly suitable for image fusion, as well as in three-dimensional exposures and in therapy planning and implementation.

DESCRIPTION OF THE DRAWINGS

FIG. 1 schematically illustrates a device for implementation of an imaging diagnostic method with two medical-technical apparatuses in accordance with the invention.

FIG. 2 is a cross-section exposure of a tissue sample to be examined as well as a recumbent board with a marking in a first embodiment, as a profiled structure on the recumbent board.

FIG. 3 is an exposure generated with the device according to FIG. 1 as well as a superimposed, corrected exposure.

DESCRIPTION OF THE PREFERRED EMBODIMENTS

Figure 4:
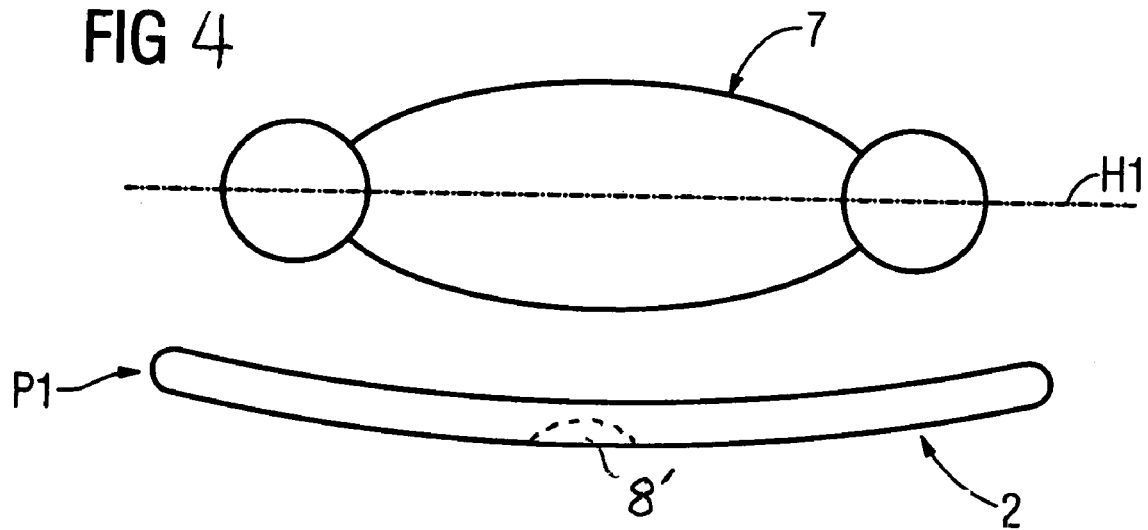
FIG. 4 is a cross-section of the recumbent board with a marking in a second embodiment, as a profiled structured in the recumbent board.

A medical-technical apparatus 1 according to FIG. 1 has a recumbent board 2 arranged on a carrier structure 3, having a base 4, such that it can be displaced in the longitudinal direction L. The recumbent board 2 can additionally exhibit further degrees of freedom (not shown). As long as the recumbent board 2 is not mechanically loaded, it is located in one plane (designated with E). A fixed point of the recumbent board 2 on the carrier structure 3 is designated with F. Given a mechanical load of the recumbent board 2 due to its inherent weight as well as in particular due to a patient (not shown in FIG. 1), the recumbent board 2 deflects (as shown in an exaggerated manner in FIG. 1). Typical deflections occur in the range of up to approximately 20 mm. The recumbent board 2 extends over a first scan region S1 of a first medical-technical apparatus 5 and over a second scan region S2 of a second medical-technical apparatus 6.

The apparatuses 5 and 6 can be any apparatuses that are suitable for imaging diagnostic methods. The apparatuses 5 and 6 can embody imaging modalities such as x-ray-techniques, magnetic resonance (MR), position emission tomography (PET) as well as single photon emission computer tomography (SPECT). In the exemplary embodiment according to FIG. 1, the first medical-technical apparatus 5 is a PET apparatus and the second medical-technical apparatus 6 is an x-ray computed tomography apparatus. Each of the medical-technical apparatuses 5, 6 is generally designated as a tomography apparatus, the exposures generated with them as tomograms. Depending on the apparatus, the generation of topograms can also be possible. The patient is moved through both tomography apparatuses 5 and 6 such that exposures of one and the same body region to be examined are generated in both tomography apparatuses 5 and 6.

The exposures of a cross-section region of the tissue to be examined that are generated in both tomography apparatuses 5, 6 are superimposed after the examination, meaning that an image fusion occurs. Given such image fusion, a precise knowledge of the vertical position of the recumbent board 2 during the examination is of particular importance. In the computed tomography apparatus 6, the cross-section of the recumbent board 2 in the tomogram can be detected without further measures, if applicable after suitable selection of the scan protocol. However, this does not apply for the PET tomogram of the first apparatus 5. The recumbent board 2 is not detectably imaged by this apparatus 5.

The section of the recumbent board 2 situated in the first scan plane S1 is designated Q1 and the section in the second scan plane S2 is designated Q2 and are respectively marked by a circle and a cross in FIG. 1. The known position of the fixed point F as well as the directly-detectable position of the section Q2 in the second scan plane S2 are used to automatically determine the position of the first section Q1 in the first scan plane S1 by calculation, taking into account the given mechanical properties of the recumbent board 2. Despite the omission of a direct measurement of the position of the recumbent board 2 in the first scan plane S1, the position of the recumbent board 2 and, therewith of the patient in the first scan plane S1, can be determined with high precision.

FIG. 2 shows a preferred embodiment of the recumbent board 2 in cross-section. A patient 7 located on the recumbent board 2 is further indicated in this representation. On its underside the recumbent board 2 has a central profile projection 8 that extends perpendicular to the shown plane in the longitudinal direction L, i.e. in the movement direction of the recumbent board 2. The profile projection 8, generally designated as a profile structure or marking structure, makes the exact determination of the position of the recumbent board 2 in the diagnostic exposure easier and preferably also has (in a non-detectable manner) structures along the movement direction L. A horizontal plane (shown in a dash-dot manner in FIG. 2) running horizontally and centrally through the patient 7 is designated as a real height plane or first plane H1. The recumbent board 2 loaded by the weight of the patient 7 is located in the a real position (designated with P1) in FIG. 2.

FIG. 3 shows two superimposed exposures of a cross-section of the patient 7 (as well as of the recumbent board 2) that are displaced linearly relative to one another. The lower exposure in the representation with the patient 7 located in the first plane H1 and the recumbent board 2 located in the real position H1 essentially corresponds to the arrangement according to FIG. 2, whereby the profile projection 8 is not shown. This arrangement is actually acquired with a medical-technical apparatus (for example the computer tomograph 6), and thus shows the raw data acquired in the imaging diagnosis. If the recumbent board 2 were not mechanically loaded (as indicated by the plane E in FIG. 1), the patient 7 would be situated in a second height plane H2 (also designated as a desired height plane). The corresponding position of the recumbent board 2 is designated as a desired position P2.

Figure 5:
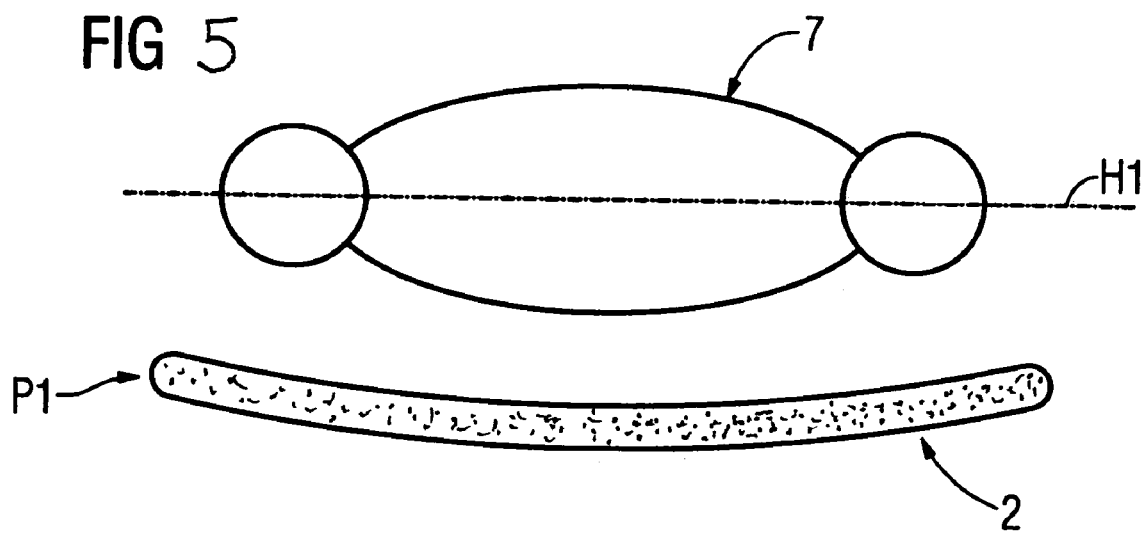
FIG. 5 is a cross-section of the recumbent board with a marking in a third embodiment, as material uniformly distributed throughout the recumbent board.

FIG. 4 shows a further embodiment of the recumbent board 2, wherein the marking is formed as a profile 8' in the recumbent board. FIG. 5 shows a further embodiment of the recumbent board 2 wherein the marking is formed by material that is uniformly distributed within the recumbent board 2. In FIG. 5, the distribution of this material is schematically indicated by stippling, but it will be understood that the material is embodied in the entirety of the material forming the recumbent board 2 and is not actually punctiform according to the stippling.

In order to be able to further process the acquired image, in particular to fuse it with other images acquired in further imaging modalities, the patient 7 ideally should be located in the second height plane H2 and the recumbent board 2 should be located in the desired position P2. In the simplest shown case, this is achieved by image processing in that the original exposure (in which the patient is located in the first height plane H1 and the recumbent board 2 is located in the real position P1) is linearly displaced by means of calculation. Insofar as a deviation of the recumbent board 2 from its desired position P2 is not detected at one coordinate, a rotation of the acquired image around arbitrary spatial axes as well as a combination of a translation operation and a rotation operation is likewise possible. The further processing of data can also refer to sinograms acquired with medical-technical apparatuses 5, 6 or data in Fourier space as raw data.

Although modifications and changes may be suggested by those skilled in the art, it is the intention of the inventors to embody within the patent warranted hereon all changes and modifications as reasonably and properly come within the scope of their contribution to the art.

I claim:

1. A method for identifying a position of a recumbent patient board in a medical image, comprising the steps of:

moving a patient on a recumbent patient board in succession through a first medical imaging apparatus and a second medical imaging apparatus, said first medical imaging apparatus operating according to a first imaging modality and said second medical imaging apparatus operating according to a second imaging modality, so that said first and second medical imaging apparatuses have different detection capabilities;

physically embodying material in or on said recumbent patient board that enhances an ability to detect said recumbent patient board with the detection capability of said second medical imaging apparatus, and said material not being detectable with the detection capability of said first medical imaging apparatus;

while horizontally moving the patient on the recumbent patient board in succession through said first and second medical imaging apparatuses, obtaining an exposure of the examination subject and a portion of the recumbent patient board with each of said first and second medical imaging apparatuses, said board with said examination subject thereon being subject to vertical deflection, due to loading of the board, from an expected position of the board;

using only said section of said board that is visible in the exposure obtained with said second medical imaging apparatus, automatically analyzing, in a processor, said exposure obtained with said second medical imaging apparatus to identify a real position of said section of said board and, in said processor, automatically comparing said real position with said expected position to identify a deviation of said real position from said expected position in the exposure obtained with said first medical imaging apparatus; and in said processor, automatically modifying said exposure obtained with said first medical imaging apparatus for said deviation, to obtain a corrected exposure, and providing said corrected exposure as an output from said processor.

2. A method as claimed in claim 1 comprising operating said first medical imaging apparatus according to a PET imaging modality.

3. A method as claimed in claim 2 comprising operating said second medical imaging apparatus with an imaging modality selected from the group consisting of magnetic resonance tomography, x-ray radiography, and computed tomography.

4. A method as claimed in claim 1 comprising distributing said material within said board.

5. A method as claimed in claim 1 comprising forming a marking, detectable in said exposure, on said board with said material.

6. A method as claimed in claim 1 comprising forming a marking, detectable in said exposure, in said board with said material.

7. A method as claimed in claim 1 comprising providing said board with a profiled projection that is detectable in said exposure.

8. A method as claimed in claim 1 wherein the step of modifying said exposure comprises linearly displacing an image of said board in said exposure dependent on said deviation.

9. A method as claimed in claim 1 comprising obtaining a three-dimensional exposure as said exposure, and wherein the step of modifying said exposure comprises three-dimensionally modifying said exposure to correct for said deviation.

10. A method as claimed in claim 1 comprising providing said board with a marking that is detectable in said exposure obtained with said second imaging apparatus, and obtaining a plurality of exposures of said tissue and said board as said board moves through said scan region of said second imaging apparatus with said examination subject thereon, and determining whether a relative speed between said board and said scan region is non-uniform by detecting said marking in each of said plurality of exposures, and if said relative speed is non-uniform, using said non-uniform relative speed to modify said exposure to correct a distortion in said exposures caused by said non-constant speed.

11. A method as claimed in claim 10 comprising calculating a three-dimensional image from said plurality of exposures, and using said marking structure detected in each of said plurality of exposures to modify each of said exposures to correct said distortion by correcting for deviation of said non-uniform movement from a uniform movement.

* * * * *